United States Patent

Köchli

Patent Number: 5,121,773
Date of Patent: Jun. 16, 1992

[54] PROCESS FOR DRAWING OFF A MILK SAMPLE

[75] Inventor: Heinrich Köchli, Neerach, Switzerland

[73] Assignee: Ewison AG, Oberburg, Switzerland

[21] Appl. No.: 585,430

[22] Filed: Sep. 20, 1990

[30] Foreign Application Priority Data

Sep. 25, 1989 [CH] Switzerland .................. 3473/89

[51] Int. Cl.⁵ .................. G01N 31/02; G01N 1/14
[52] U.S. Cl. .................. 141/1; 222/571; 141/130; 141/83; 141/127
[58] Field of Search .................. 141/1,4,5,11,86,130, 141/7, 85, 116, 127, 83; 222/571

[56] References Cited

U.S. PATENT DOCUMENTS

| | | | |
|---|---|---|---|
| 3,184,973 | 5/1965 | Bradley | 73/422 |
| 3,386,382 | 6/1968 | Schuette et al. | 141/116 X |
| 3,511,468 | 5/1970 | Young | 222/571 X |
| 3,970,119 | 7/1976 | Doane | 141/1 |
| 4,170,798 | 10/1979 | Krumdieck | 141/130 X |
| 4,274,453 | 6/1981 | Lee | 141/1 |
| 4,387,076 | 6/1983 | Cabrera et al. | 141/130 X |
| 4,403,764 | 9/1983 | Repplinger | 222/571 X |
| 4,501,161 | 2/1985 | Endo | 73/863 |
| 4,609,017 | 9/1986 | Coulter et al. | 141/1 |

FOREIGN PATENT DOCUMENTS 3502858 10/1985 Fed. Rep. of Germany .

OTHER PUBLICATIONS

DMZ Deutsche Molkerei-Zeitung, Nr.44, Oct. 1984, pp. 1504-1510 Landre "Grenzen der Entwicklung Automatischer Probenahmegeräte".

Primary Examiner—Ernest G. Cusick
Attorney, Agent, or Firm—Townsend and Townsend

[57] ABSTRACT

In the equipment for drawing off milk samples from a milk conveyor pipe (1), in order to remove any milk remaining from the previous supplier and adhering within the suction pipe (5) and the injection syringe (6), before taking a sample from the current supplier the suction pipe (5) and the injection syringe (6) are filled with milk and after being completely filled they are emptied again by pumping the milk back into the conveyor pipe (1). The process of filling to fullness is monitored by a control means (9) which operates a hose pump (7) such that only the exact quantity of milk required to fill the suction pipe (5) and the injection syringe (6) is conveyed. Only after this filling and emptying procedure is the injection syringe (6) inserted into a sampling bottle (8) disposed on a dish (15) which can be raised. A holding down device (16, 17, 18) guarantees perfect withdrawl of the injection syringe (6) from the sampling bottle (8) when the dish (15) is lowered at the end of the sampling. The equipment is charactized by the simple process permitting the left-over milk to be removed from the suction pipe and the injection syringe, thus preventing carry-overs.

12 Claims, 2 Drawing Sheets

PROCESS FOR DRAWING OFF A MILK SAMPLE

BACKGROUND OF THE INVENTION

This invention relates to a process and a device for drawing off a milk sample from a milk conveyor pipe and equipment for drawing off a sample, particularly on milk collection lorries.

The demands made of automatic equipment for taking milk samples are high. The equipment must function perfectly so that carry-over errors are minimal and samples are taken in the correct quantitative proportion. A quality-payment system, where milk samples are taken by hand with a ladle and mixer is not above all doubt since carry-over errors may, for example, occur or there may be a delay between taking the sample and collecting the milk.

After each sampling process, a certain amount of milk remains as liquid which adheres and accumulates on the wetted inner surfaces of the automatic sampling equipment. This remaining milk is rinsed away again by the next sampling process, is mixed with the following milk and partially carried into the sample bottle as a so-called carry-over. Carry-over errors can be minimized by means of special measures relating to the construction and technical functioning of automatic milk sampling equipment Moreover, it is important that representative samples are taken, a representative sample being a portion of the milk whose features correspond to that of the whole quantity from which the sample is taken. It is also possible by means of measures relating to the construction and technical functioning, to keep the representativity high.

One known embodiment of a device for the direct transfer of partial quantites of milk from a milk conveyor pipe into a sample bottle is disclosed in the German published patent application DE 36 27 849. This device functions such that a sample bottle is affixed to a peripheral opening in the milk conveyor pipe in an airtight manner using a flexible sealing part so that there is form and/or force locking. A fill-up syringe and an air-discharge syringe are disposed in the conveyor pipe and are movable transverse to the conveyor pipe and can be inserted into the sample bottle to take up a position for drawing off a sample. Prior to insertion in the sample bottle, the syringes are in the so-called rinse position in the milk flow of the conveyor pipe. By means of a shutting element which also projects into the milk conveyor pipe and is diposed such that it is movable therein, the timing of the sampling can be controlled. The disadvantages of this known construction are in the movable parts which are difficult to clean in the milk conveyor pipe, and which also give rise to problems of airtightness. If a vacuum occurs when conveying the milk in the milk conveyor pipe, milk from the sample bottle can flow back into the milk conveyor pipe. This impairs representative sampling.

Another known embodiment of a device for drawing off milk samples is disclosed in the German published patent application DE 35 02 858. The device comprises a draw-off pipe, inserted into the milk conveyor pipe, through which milk is drawn off into the sample bottle by means of a hose pump driven by rhythmic impulses. According to the expected quantity of milk, the length and/or frequency of the impulses can be changed in order to achieve a representative sample. Milk can be prevented from being carried over from a previous sampling to the next sample by automatically activating the sample draw-off pipe for a short time as soon as the conveyor pipe is filled with milk, in order to rinse the milk draw-off pipe free of remaining adhering milk, this rinse milk being led away and not taken into the sample bottle. Disadvantageous additional structural expenditure is required by this device to activate the sample draw-off pipe and to capture the rinse milk, for which a funnel is used.

SUMMARY OF THE INVENTION

It is the object of the present invention to overcome the above-mentioned disadvantages. In accordance with the invention, a process and a device for drawing off a milk sample, from a milk conveyor pipe will now be proposed. Special features of equipment for drawing off a sample, particularly on milk collection lorries, with a device according to the invention are also disclosed. Using the suggested process and the device for carrying out the process, the device can be cleared of the milk left from the previous supplier in a easy, economic way. The device is of a simple construction, and there are no special sealing and cleansing problems. The features of the equipment for drawing off the sample ensure that the possibility of drawing off an unrepresentative sample is practically excluded.

Using an embodiment example and diagrams, the invention will now be described in more detail:

DESCRIPTION OF THE PREFERRED EMBODIMENTS

Figure 1:
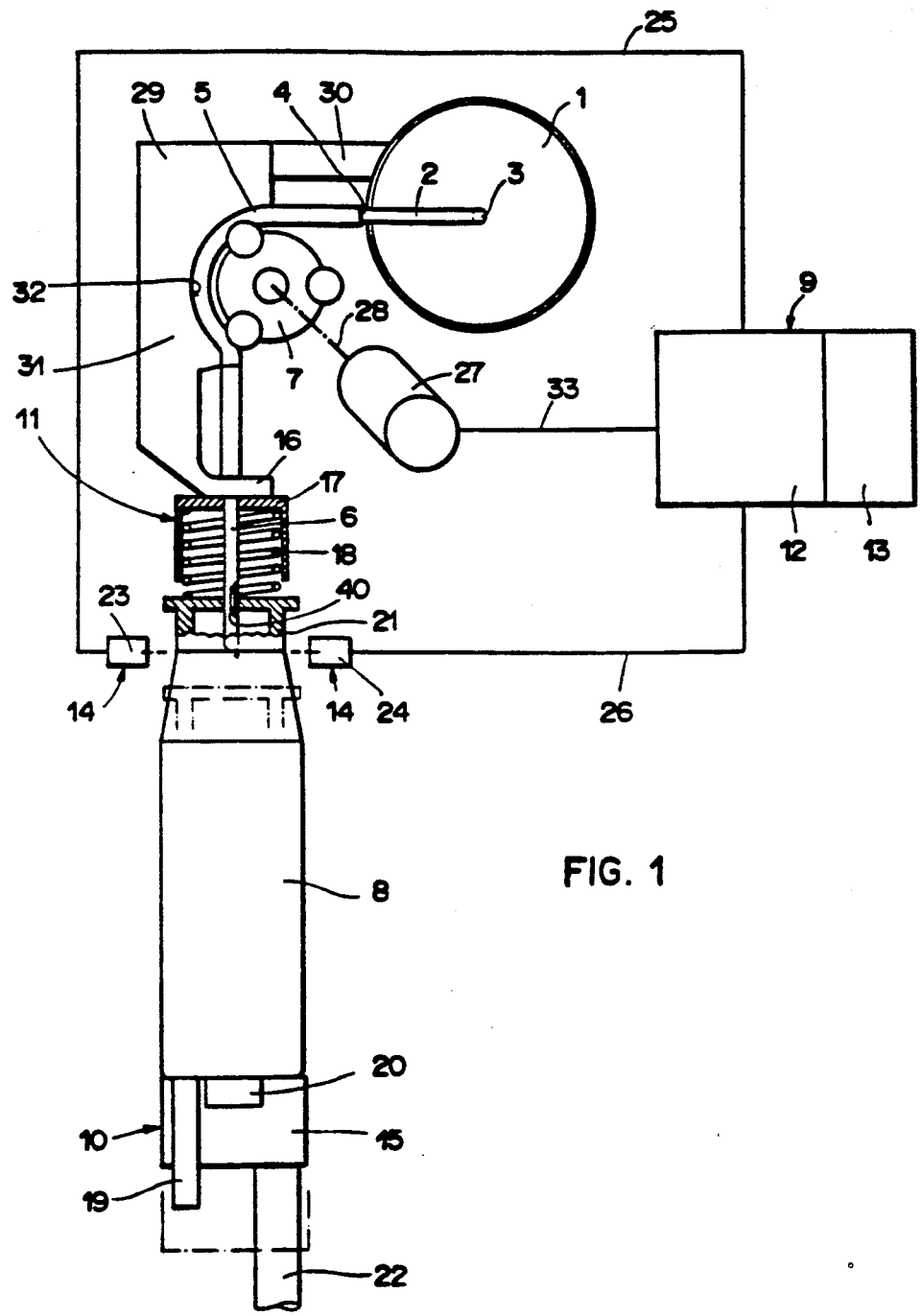
FIG. 1 shows a device in accordance with the invention on a milk conveyor pipe.

Reference 1 in FIG. 1 shows a cross-section of the milk conveyor pipe intended to connect a milk supplier's milk storage tank which is not shown, with a milk collection lorry. A suction connection piece 2 is inserted radially into the milk conveyor pipe 1, the end 3 of the connection piece which projects into the milk conveyor pipe 1 being bent against the direction of flow of the milk and having an aperture. The end 3 is preferably disposed in the region of the center of the milk conveyor pipe 1. The other end 4 of the suction connection piece 2 leads into a flexible suction pipe 5 whose end which is turned away from the connection piece bears an injection syringe 6. An arm 30 of an L-shaped support 29 is affixed externally to the milk conveyor pipe and runs essentially parallel to the suction connection piece 2. The other arm 31 of the L-shaped support is essentially at a right angle to the arm 30. The inner surface 32 of the support 29 is shaped as a partial circle in order to guide the flexible suction pipe 5. A hose pump 7 known per se interacts with the flexible suction pipe in the inner surface shaped as a partial circle. The hose pump 7 is driven by a motor 27 via a shaft 28. At the end of the arm 31 there is a support foot 16 on whose side turned away from the arm 31 is affixed a cup-shaped spring cage 17. A spiral spring 18 is inserted from the lower open end of the spring cage 17 into the latter and held in the cage in a way which is not shown. By means of conveyor equipment which is not shown in this figure either, a sample bottle 8, disposed on a dish which can be raised or lowered, with a flexible and self-sealing seal 21 disposed at the upper end, presses against the spiral spring 18 whilst the said injection syringe pierces the seal when the dish 15 is raised.

The dish 15, which can be raised and lowered hydraulically or preferably pneumatically over a cylinder 22 which is only partially shown, comprises a detection element 19 for detecting a correctly positioned sample bottle 8 on the dish and a retaining element 20, preferably a permanent or electromagnet for retaining the bottle. In this case it is obvious that the base of the bottle at least is made of a magnetic material. The dish 15, the detection element 19, which may for example consist of a capacitive approach indicator, the retaining element 20 and the pneumatic cylinder 22 are designated as a whole as conveyor means by the reference number 10. When the dish 15 is lowered, the spiral spring 18 supports the withdrawal process of the injection syringe 6 from the bottle seal 21. The support foot 16 with the spring cage 17 and the spring 18 are designated as a whole as a holding down device of withdrawal means 11. In a particular form of embodiment a sensor 14, preferably a light barrier with a light transmitter and a light receiver, may be disposed at the lower end of the immovable injection syringe 6. The light transmitter 23 is connected to control means 9 via a first multiconductor line 25. A similar connection 26 exists between the light receiver and the control means 9. The latter, which comprises a calculating device 12 with integral memory 13, serves amongst other things to control the hose pump 7. To this end, the motor 27 is connected with the control means 9 via a third electric line.

This device, which is used below to illustrate in detail the process in accordance with the invention, is characterized by its simple construction which guarantees reliable operation.

In contrast to other known embodiments it is remarkable that the injection syringe 6 is disposed such that it is immovable. To remove milk which is left behind by the previous supplier, milk which could, in particular, adhere to the suction pipe 5 and the injection syringe 2, according to the process of the invention the following procedure is undertaken: when a transfer of milk is underway, as soon as the conveyor pipe 1 is filled with the milk of the current supplier the calculating device 12 switches on the motor 27 and the hose pump 7, via the third electric line 33. The pump begins to pump milk out of the conveyor line via the suction connection piece 2 into the suction pipe 5 and into the injection syringe 6. At this point, the dish 15 with the sample bottle 8 which is already disposed thereon, is still in its lowered position, which is shown in FIG. 1 by broken lines. The injection syringe 6 does not yet have any contact with the bottle seal 21. The hose pump 7 pumps milk into the suction pipe and the injection syringe until their volume is completely filled with milk. In a first, preferred embodiment there is no sensor 14 foreseen to monitor the level. The known volumes of the suction pipe 5 and the injection syringe 6 are stored in the memory 13 which is integral to the calculating device 12. By means of a software program the pump is operated at an appropriate number of revolutions corresponding to a certain milk conveyance rate until exactly the quantity of milk required to fill the said volumes has been transferred. As soon as the said volumes are completely full, the hose pump 7 is stopped briefly and then immediately operated in the opposite direction. The milk previously pumped into the suction pipe 5 and the injection syringe 6 is now pumped back into the conveyor pipe. Thus it is possible to remove milk remaining from a previous supplier from the said volumes in an extremely simple way. No milk is lost and it is unnecessary to apply flasks to collect rinse milk or to swing the injection syringe over a container to release rinse milk. Only after completion of this described rinsing procedure, which only lasts a few tenths of a second, is the sample bottle 8 raised by the dish 15. The injection syringe 6 pierces the bottle seal 21. The spiral spring then presses against the upper end of the bottle seal to support the retention of the bottle 8 by the retaining element 20. The procedure of actually drawing off a sample can now be started. To this end, the hose pump 7 is switched on in the appropriate direction. Ideally, the sampling should be carried out proportionally over the whole of the milk conveying process. Using the quantity of milk which is to be collected, a quantity which has been entered into the calculating device 12, the latter calculates the amount which the hose pump 7 is required to convey. The time lost—at the most, 0.5 seconds—by the described rinsing procedure is compensated for at the point of sampling since the hose pump 7 first pumps slightly more than would be required. At the end of the sampling, (the volumes of the suction pipe 5 and the injection syringe 1 have been emptied), the dish 15 with the sample bottle 8 is lowered. When this takes place, the injection syringe 6 is withdrawn from the flexible, self-closing bottle seal. This withdrawal process is aided by the spiral spring 18 of the holding down equipment 16, 17, 18.

Naturally, when filling and emptying the volumes of the suction pipe 5 and the injection syringe 6 it would also be possible to monitor particularly the level using a sensor, which is indicated by the reference 14. This could preferably be done with a light barrier so that the beam of light emitted from the light transmitter 23 is interrupted as soon as a drop of milk appears in the opening of the injection syringe 6. The light receiver 24 could relay this interruption in the beam of light back to the calculating device 12, which would immediately stop the hose pump.

With this device with a hose pump 7 it is not possible for milk to get back into the conveyor pipe 1 from the sample bottle 8 if a vacuum occurs in the conveyor pipe 1. Moreover, mention should also be made of the fact that when filling the sample bottle 8, the air contained therein can escape via a slit which is disposed on the outside of the injection syringe 6.

Figure 2:
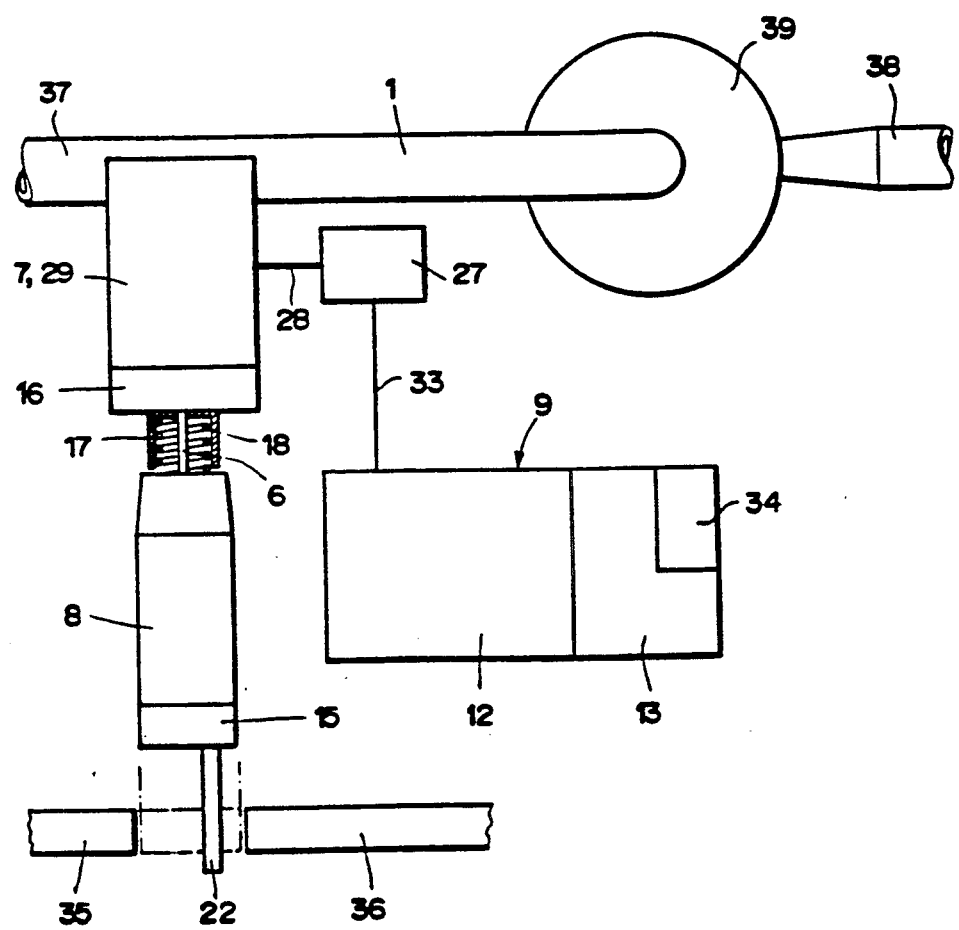
FIG. 2 shows the essential parts of sampling equipment, in particular on milk collection lorries with a device according to FIG. 1.

Sampling equipment where the previously described device in accordance with the invention for drawing off milk samples is attached to the conveyor pipe 1, is shown in FIG. 2. One end 37 of the conveyor pipe 1 is connected with a hose which is not shown and which is intended to be inserted into the milk supplier's storage tank. The other end 38 of the milk conveyor pipe 1 is connected with the tank—not shown either—of the milk collection lorry, on which the sampling equipment is preferably disposed. A feed pump 39, which is also controlled by the controlling means 9 in a way not further shown, conveys the milk through the milk conveyor pipe 1. 35 and 36 are conveyor means which operate in a known way, for example using conveyor belts, and are intended to bring sample bottles up to and away from the dish 15 in its lowered position.

In order to obtain representative samples, it has to date been usual to enter manually via a keyboard or other switching equipment into the control means 9 the expected quantity of milk at each supplier. Since a calculating device 12 and a memory 13 are already present in the device described, it is advantageous to store the milk quantity expected from any supplier in the memory capacity 34 intended therefor. The operator must then merely enter the supplier's code into the calculation means which nowadays is preferably done with a coded card via a card reader which is not shown but which is connected with the calculating device 12. This system excludes the possibility of wrong details concerning milk quantities and it is hardly possible to draw off unrepresentative samples.

What is claimed is:

1. A process for drawing off a milk sample from a milk conveyor pipe into which is inserted one end of a suction connection piece, a suction pipe having an injection syringe attached thereto being connected to another end of the connection piece, said process including rinsing a sampling path through the suction pipe and the syringe to avoid contamination of the milk sample with milk residue in the path from a previous sample, the process comprising the steps of:

completely filling a pre-calculated volume of the suction pipe and the injection syringe with milk from the milk conveyor pipe, while preventing the escape of any milk from the injection syringe;

returning the milk previously filled in said volume of the suction pipe and the injection syringe by conveying the milk in said volume through the suction pipe back into the milk conveyor pipe;

inserting the injection syringe into a previously positioned sample bottle; and thereafter filling said sample bottle with milk from the conveyor pipe.

2. A process according to claim 1, wherein a hose pump interacting with a calculating device controls said filling and returning steps, and further comprising the steps of:

activating the hose pump to induce a flow of milk in the suction pipe in a first direction at a rate corresponding to a fixed conveying capacity for a pre-calculated time required to fill said volume; and reactivating the hose pump to induce a flow of milk in the suction pipe in a second direction, opposite to said first direction, at said rate for a time equal to at least said pre-calculated time.

3. A process according to claim 1, wherein said inserting step comprises the steps of maintaining the injection syringe stationary and displacing said sample bottle towards the injection syringe.

4. A process according to claim 1, wherein said filling and returning steps for rinsing purposes require no more than 0.5 seconds which is compensated for by a temporary increase in the milk flow rate induced by the hose pump during the reactivating step.

5. A device for drawing off a milk sample from a milk conveyor pipe comprising:

a suction connection piece having one end in fluid communication with the conveyor pipe;

a suction pipe having one end in fluid communication with another end of said suction connection piece;

an immovably mounted injection syringe in fluid communication with another end of said suction pipe;

a hose pump interacting with said suction pipe for inducing milk to flow therethrough and in both directions of the suction pipe;

control means, including a calculating means and a memory means, operatively connected to and controlling the operation of said hose pump; and movement means for raising a sample bottle toward said immovably disposed injection syringe so that the syringe extends into the bottle and lowering the bottle so that the syringe is outside the bottle;

wherein said memory means stores a value representative of the volume of said suction pipe and said injection syringe, and wherein said calculating means controls the direction and the pumping rate of said hose pump to fill and subsequently empty said volumes of said suction pipe and said injection syringe while milk flows in the milk conveying pipe.

6. A device according to claim 5, wherein said calculating means is adapted to control the operation of the pump while the milk flows in the conveying pipe so that the milk sample is taken proportionally to the entire amount of milk flowing through the conveying pipe from a given milk supplier, whereby the milk sample is representative of said entire amount of milk from the given milk supplier.

7. A device according to claim 5, including a sensor operatively coupled with said control means for detecting when said volumes of the suction pipe an the syringe are completely full.

8. A device according to claim 5, wherein said movement means comprises a raisable dish supporting the bottle, and a holding down device holding the bottle on the dish.

9. A device according to claim 8, wherein said dish is pneumatically raisable and includes means for determining a presence of a sample bottle and means for retaining said bottle.

10. A device according to claim 8, wherein said holding down device includes a spring means positioned to apply a force to the bottle brining the bottle towards the dish when said sample bottle is in a raised position.

11. A device for drawing off a milk sample from a milk conveyor pipe, particularly on milk collection lorries, comprising:

a suction connection piece having one end in fluid communication with the conveyor pipe;

a suction pipe having one end in fluid communication with another end of the suction connection piece;

an immovably mounted injection syringe in fluid communication with another end of said suction pipe;

a hose pump interacting with said suction pipe for inducing and controlling the flow rate and direction in the suction pipe; and control means, including calculating means and memory means, operatively connected to and controlling the operation of said hose pump; said control means including means for recording the quantity of milk from individual suppliers that is anticipated to flow through the conveyor pipe.

12. A device according to claim 11, wherein said control means controls the milk conveying rate of said hose pump to withdraw a proportional sample of milk from the conveyor pipe as a function of the quantity of milk anticipated from a given supplier.

* * * * *